US00PP12061P2

(12) United States Plant Patent
de Groot

(10) Patent No.: US PP12,061 P2
(45) Date of Patent: Aug. 21, 2001

(54) GARLIC PLANT NAMED 'CINDY'

(75) Inventor: Henk de Groot, Broek op Langedijk (NL)

(73) Assignee: De Groot & Slot Beheer B.V., Heerhugowaard (NL)

( * ) Notice: Subject to any disclaimer, the term of this patent is extended or adjusted under 35 U.S.C. 154(b) by 0 days.

(21) Appl. No.: 09/325,352

(22) Filed: Jun. 4, 1999

(51) Int. Cl.[7] ..... A01H 5/00

(52) U.S. Cl. ..... Plt./258
(58) Field of Search ..... Plt./258

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of Garlic plant named 'Cindy' characterized by the early harvesting of the plant, high yield of bulbs, healthy vegetation, presence of flower scape, distinctive bulb form and size, vigorous foliage that develops quicker and has more volume than comparative cultivars, and distinctive color of the bulb and cloves.

4 Drawing Sheets

BACKGROUND OF THE INVENTION

The present invention relates to a new and distinct cultivar of garlic plant, botanically known as *Allium sativum L.* and hereinafter referred to by the cultivar name 'Cindy'.

'Cindy' is a product of a planned breeding program which had the objective of creating new garlic cultivars having early harvesting capabilities, high yield potential, regular clove arrangements, healthy plant material and seed-propagated garlic cultivation.

'Cindy' was originated from an open pollination made in a controlled breeding program, which began in 1987 in Broek op Langedijk, the Netherlands. The parent lines were unnamed seedlings of Russian Republic origin. During the breeding program, several selections were made within the progeny of the open pollination.

'Cindy' was discovered and selected as one plant growing among the group of selected plants by the inventor, Henk de Groot, in 1993 in a controlled environment in Broek op Langedijk, the Netherlands. Plants of 'Cindy' differ from plants of the parental cultivars, unnamed seedlings of Russian Republic origin, in that foliage of plants of 'Cindy' develops quicker and has more volume than plants of the parental cultivars.

The first act of asexual reproduction of 'Cindy' was accomplished by the inventor in which cloves were taken from the initial selection in August 1993 in a controlled environment in Broek op Langedijk, the Netherlands. Horticultural examination of asexually reproduced plants of 'Cindy' initiated in 1994 has demonstrated that the combination of characteristics as herein disclosed for 'Cindy' are firmly fixed and reproduces true to type through successive generations of asexual reproduction.

BRIEF DESCRIPTION OF THE INVENTION

The following traits have been repeatedly observed and are determined to be basic characteristics of 'Cindy' which in combination distinguish this garlic as a new and distinct cultivar:

1. Early harvesting of the plant;
2. High yield of bulbs;
3. Healthy vegetation;

4. Presence of flower scape;
5. Distinctive bulb form and size;
6. Vigorous foliage that develops quicker and has more volume than comparative cultivars; and
7. Distinctive color of the bulb and cloves.

'Cindy' has not been observed under all possible environmental conditions. The phenotype of the new cultivar may vary significantly with variations in environment such as daylength, temperature, soil condition, humidity, fertilization and date of planting without any change in genotype of the cultivar. The following observations, measurements, and comparisons describe plants grown in Broek op Langedijk, the Netherlands under conditions that approximate those generally used in commercial practice. The age of the plants described is 9 months after planting.

Of the many commercial cultivars known to the present inventor, the most similar in comparison to 'Cindy' is 'Thermidrome' (unpatented). In comparison to 'Thermidrome', 'Cindy' has a similar bulb color but demonstrates significant differences in presence of the scale, bigger-sized bulbs, healthier leaves, arrangement and size of the cloves, earlier harvesting period and greater plant height.

The following chart represents a comparison, based on Dutch cultivation conditions, of the principle variety characteristics of 'Cindy' and 3 main commercial varieties:

| Variety characteristics | 'Thermidrome' | 'California Early' | 'Germidour' | 'Cindy' |
|---|---|---|---|---|
| Emergence speed after Planting | Slow | slow | fast | rather slow approximately 8 weeks |
| Foliage Type | Erect | erect | bending up to hanging | leaves have a tendency to bend |

-continued

| Variety characteristics | 'Thermidrome' | 'California Early' | 'Germidour' | 'Cindy' |
|---|---|---|---|---|
| Foliage Color | Green | green | green | green RHS 137 A to 137 B for both upper and lower leaf surfaces |
| Plant Height - normal length of the foliage | 60 cm | 60 cm | 65 cm | 80 cm |
| Plant Height - maximum length of the foliage | 85 cm | 80 cm | 85 cm | 100 cm |
| Strength of the plant | Normal | normal | normal | slack |
| Susceptibility to bolt | No | no | no | 29 weeks after planting |
| Tendency for branching | very light | insensitive | insensitive | does not branch |
| Earliness (10 is fastest variety 'Melany'; difference in weeks) | 6 | 7 | 8 | 6 |
| Skin color of the bulb | White | white | pink/purple | white RHS 155 D with a pink shade |
| Skin color of the cloves | White | white | pink/purple | RHS 65 D |
| Yield in gram/bulb (average of 2 years) | 80 | 80 | 85 | 120 |
| Yield in ratio to California Early/Thermidrome | 100% | 100% | 105% | 155% |
| Average number cloves per bulb | 10 to 12 | 10 to 12 | 9 to 11 | 9 to 10 |
| Clove arrangement | Irregular | irregular | irregular | regular |
| Percentage dry matter (average of 3 years) | 40 | 39 | 39 | 42 |
| Storability | Medium 26 weeks after harvesting | medium | medium | long 35 weeks after harvesting |

In the above chart, susceptibility to bolt was measured by visual observations based upon the inventor's information from the Dutch trial field during the 1996/1997 and 1997/1998 production seasons. Earliness ('Melany' is the fastest variety with a value of 10; difference in weeks) indicates that 'Melany' (U.S. plant patent application Ser. No. 09/325,778) is considered to be the earliest variety whereby the standard is 10. Therefore, an earliness of 8, as in 'Germidour' (unpatented) for example, means that this variety is 2 weeks slower than 'Melany'. These figures are based upon the inventor's information from the Dutch trial field during the 1996/1997 and 1997/1998 production seasons.

Also, in the above chart, 'California Early' (unpatented) and 'Thermidrome' are standard cultivars in the U.S. and Europe, respectively, and can be compared with respect to yield (production weight per area). The percentages that are given for Yield in ratio to 'California Early'/'Thermidrome' indicates the relative average yield increase of the new cultivar. Dry matter was measured by means of a drying apparatus in which 25 grams of garlic material per variety was dried for 72 hours at 72° C. The percentage of dry matter was then calculated using the formula: 100×weight of material after drying/weight of same material before drying. To determine an average, this test was repeated five times for each growing season 1996/1997 and 1997/1998. Storability was measured as the relative marketable yield of garlic bulbs after certain storage periods: 4–6–8 months.

BRIEF DESCRIPTION OF THE DRAWINGS

The accompanying photographic drawings show typical plant and bulb characteristics of 'Cindy' following growth from appropriate growing conditions, with colors being as true as possible with illustrations of this type.

Sheet 1 is a side view of the plant in cultivation.

Sheet 2 shows a side view of the plant.

Sheet 3 shows a side and bottom view of the bulb.

Sheet 4 shows individual cloves within the bulb.

'Cindy' was known as "GS 214" during testing, as labeled on the photographic drawings.

DETAILED BOTANICAL DESCRIPTION

The following observations, measurements and values describe the new cultivar as grown in Broek op Langedijk, the Netherlands, under conditions which closely approximate those generally used in commercial practice. Color references are made to The Royal Horticultural Society Colour Chart (R.H.S.), except where general colors of ordinary significance are used.

Origin: Through breeding in Broek op Langedijk, the Netherlands.

Parentage: Unnamed seedlings of Russian Republic origin.

Classification:

*Botanical.*—*Allium sativum L.*

*Commercial.*—Garlic, cv. 'Cindy'.

Plant:

*Form.*—Bulbous herb.

*Height.*—Normal height of a mature plant is approximately 80 cm depending on cultivation conditions. Maximum height is approximately 100 cm. Height including umbel is approximately 110 cm, depending on cultivation conditions when grown in Broek op Langedijk, The Netherlands.

*Growth habit.*—Vigorous growth and volume (in comparison to standard variety 'California Early') after slow initiation; the time from planting a bulbet to the emerging from the soil is about 8 weeks; the plant is mature about 40 weeks from planting.

*Harvest/typical growing season.*—In one growing season only one harvest takes place. The typical growing season is from October to July in Western European climate conditions and from October to June in sub-Mediterranean conditions.

Foliage:

*Quantity.*—Approximately 14 leaves depending on cultivation conditions.

*Size.*—Maximum length is approximately 90 cm depending on cultivation conditions.

*Shape.*—Lanceolate, arched to slightly bent.

*Color.*—Green RHS 137 A to 137 B for both upper and lower leaf surfaces.

*Width.*—1–2 cm.

*Apex.*—Acute.

*Base.*—Sessile.

*Texture.*—Glossy.

Scape:
*Length.*—Approximately 150 cm depending on cultivation conditions.
*Diameter.*—Less than 1 cm.
*Color.*—RHS 137 A to 137 B.
Umbels:
*Length.*—4.5 to 5 cm.
*Diameter.*—5 cm.
*Shape.*—Bulbous with tappered appendix.
*Bracts.*—1; width 1 cm; length 3–4 cm; light green to white.
*Bulbils.*—Present more than 50, less than 200, depending on cultivation and climate conditions.
*Shape.*—Elliptical.
*Length.*—5 mm.
*Diameter.*—2 mm.
*Color.*—Brown.
*Spathe.*—Compound flowers filled with bulbils, 1.
*Size.*—Small bulbils 4 cm in diameter.
*Pedicels.*—Present, length 3 cm; diameter 1 mm; color green.
Flower bud:
*Length.*—2 mm.
*Diameter.*—1 to 2 mm.
*Shape.*—Size and form of a pin-head.
*Color.*—Light green base and white head.
Bulb:
*Shape.*—Round to spherical.
*Size.*—Averages 8 cm in diameter depending on cultivation conditions.
*Color.*—White RHS 155 D with a pink shade.
*Number of cloves.*—9 to 10.
*Clove color.*—White, (RHS 155 D) (without skin).
*Clove skin color.*—RHS 165 D.
*Average weight of bulb.*—120 grams over two years (average weight from two different years).
*Clove shape.*—Transversely in triangular shape with round edges.
*Clove length.*—3–4 cm; in longitudinal section running to a point.
*Clove diameter.*—1–2 cm at the widest part.
*Clove texture.*—Glossy with and without the skin.
*Individual weight of clove.*—Average 13 grams per clove depending on cultivation conditions.
Disease resistance: High for mildew, rust and botrytis.
Other characteristics: Dry matter averaged 42% over 3 years of research. Long storability.
Reproductive organs:
*Anthers.*—Quantity: 5–15. Size: Less than 1 mm in length. Color: Grey.
*Sigma and styles.*—Typical of the species.
*Ovaries.*—Quantity: 8 per flower. Size: 2 mm. Color: Light green and white.
*Pollen.*—None produced.
Seed: None produced.

I claim:

1. A new and distinct cultivar of garlic plant named 'Cindy', as illustrated and described.

* * * * *

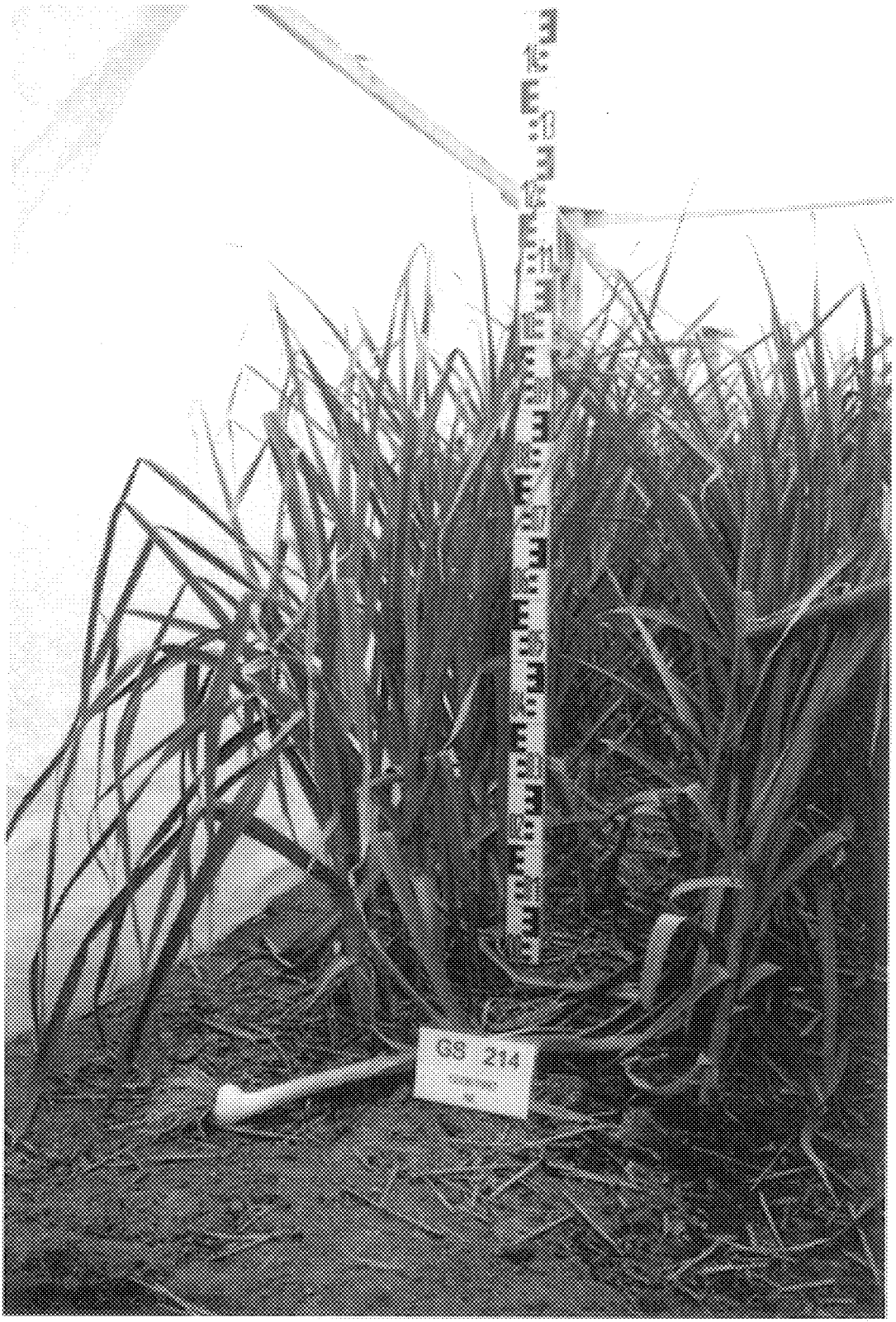
GS 214

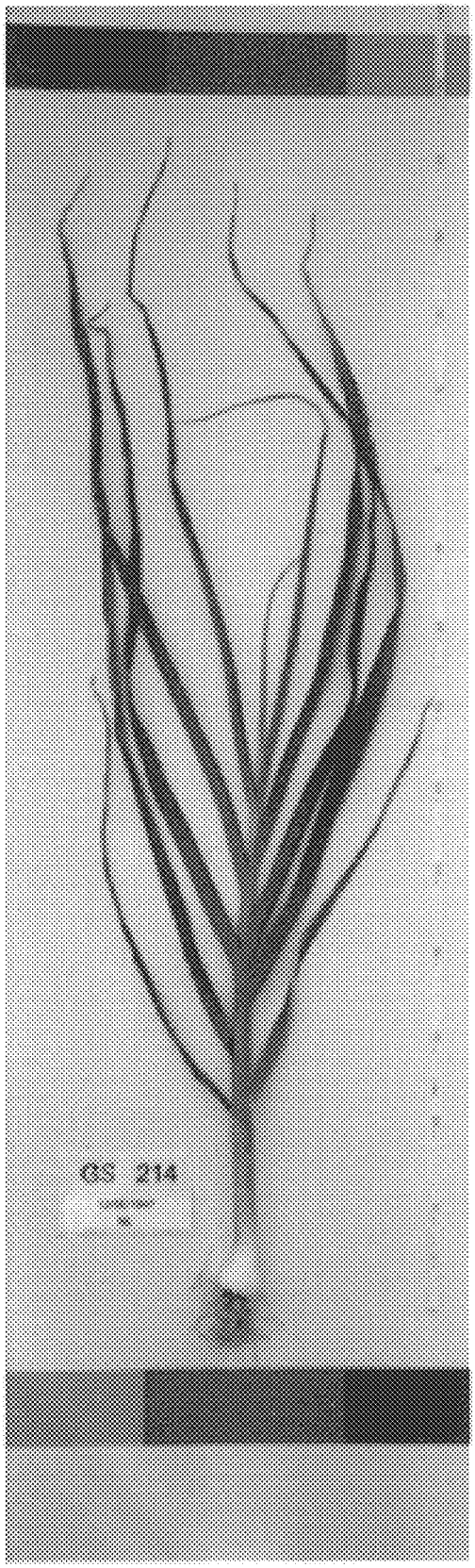
GS 214

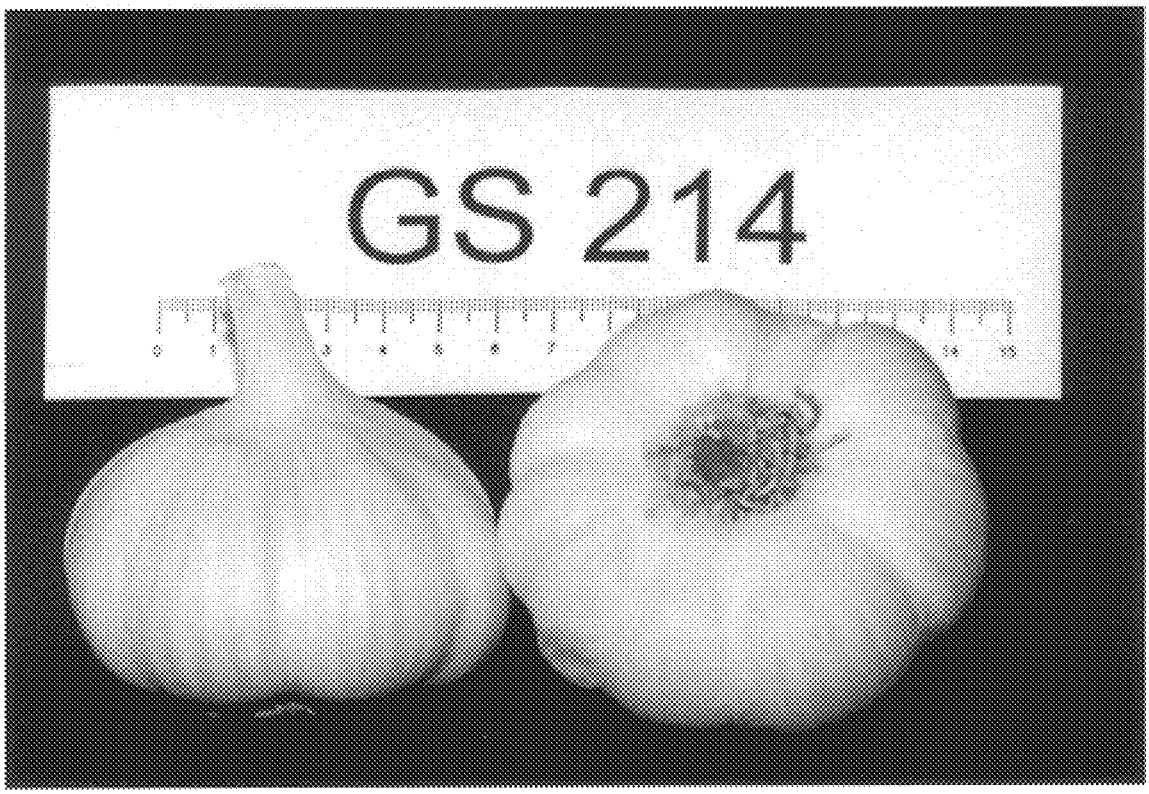
GS 214

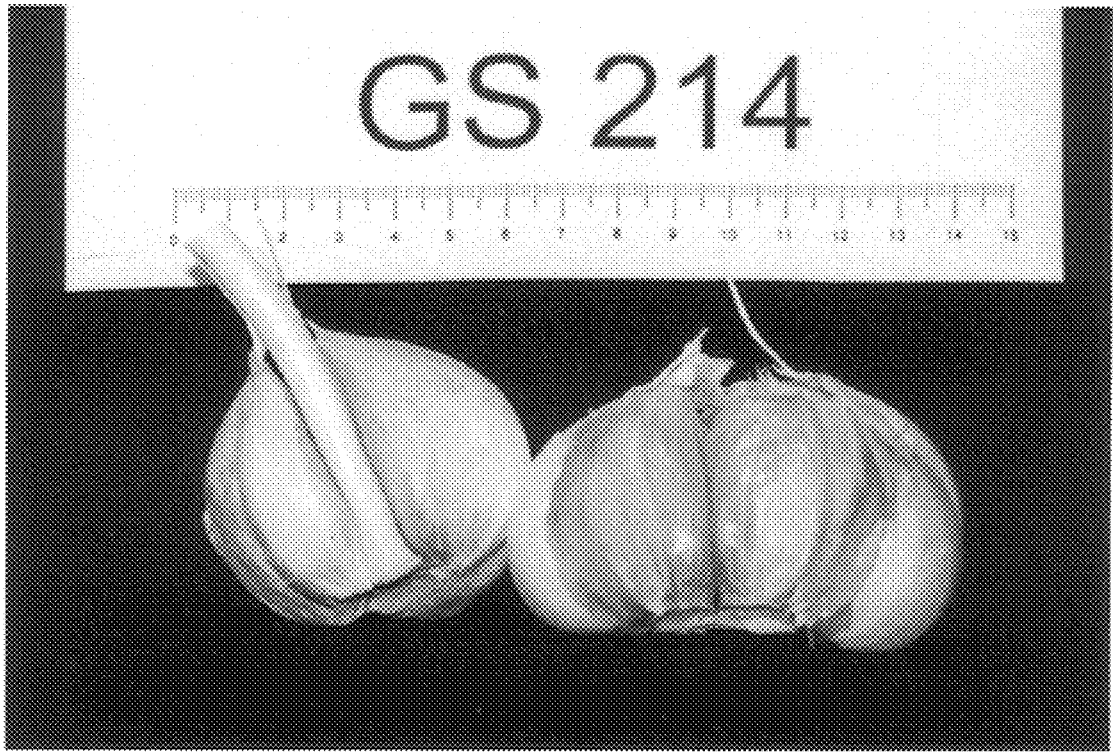
GS 214